United States Patent
Karpecki et al.

(10) Patent No.: US 11,633,101 B2
(45) Date of Patent: *Apr. 25, 2023

(54) APPARATUS FOR DIAGNOSIS OF OCULAR SURFACE DISEASE

(71) Applicant: Ophthalmic Resources LLC, Sparks, NV (US)

(72) Inventors: Paul M. Karpecki, Lexington, KY (US); Douglas K. Devries, Sparks, NV (US)

(73) Assignee: Ophthalmic Resources LLC, Sparks, NV (US)

( * ) Notice: Subject to any disclaimer, the term of this patent is extended or adjusted under 35 U.S.C. 154(b) by 104 days.

This patent is subject to a terminal disclaimer.

(21) Appl. No.: 17/237,466

(22) Filed: Apr. 22, 2021

(65) Prior Publication Data

US 2021/0235989 A1 Aug. 5, 2021

Related U.S. Application Data

(62) Division of application No. 16/033,624, filed on Jul. 12, 2018, now Pat. No. 11,013,405.

(60) Provisional application No. 62/533,360, filed on Jul. 17, 2017.

(51) Int. Cl.
| | |
|---|---|
| *A61B 5/00* | (2006.01) |
| *A61B 3/15* | (2006.01) |
| *A61B 3/00* | (2006.01) |
| *A61B 3/14* | (2006.01) |
| *H04B 1/3827* | (2015.01) |

(52) U.S. Cl.
CPC ............ *A61B 3/152* (2013.01); *A61B 3/0033* (2013.01); *A61B 3/0058* (2013.01); *A61B 3/0091* (2013.01); *A61B 3/145* (2013.01); *A61B 5/6898* (2013.01); *H04B 1/3827* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,210,554 | A * | 5/1993 | Cornsweet | A61B 3/112 351/204 |
| 2011/0242483 | A1* | 10/2011 | Shea | A61B 3/0058 351/246 |
| 2014/0285436 | A1* | 9/2014 | Wu | A61B 5/489 345/156 |

* cited by examiner

*Primary Examiner* — Joel F Brutus

(57) ABSTRACT

An apparatus for diagnosis of ocular surface disease includes an electronic tablet with an electronic display and a forward-facing camera. The camera may be placed above the screen when the device is held in landscape mode. A software app executing on the electronic tablet displays a test screen to a patient, the test screen comprising a test image and an alignment indicator. Once alignment is achieved, the patient may read the test image for a period of time, during which blink quality and quantity are tabulated. A video recorded during the test may be reviewed by a physician to confirm or modify blink quality and quantity counts during the test to diagnose ocular surface disease.

19 Claims, 3 Drawing Sheets

APPARATUS FOR DIAGNOSIS OF OCULAR SURFACE DISEASE

CROSS-REFERENCE TO RELATED APPLICATIONS

This application is a divisional application of U.S. patent application Ser. No. 16/033,624, filed on Jul. 12, 2018, which in turn claims priority from U.S. provisional patent application No. 62/533,360, filed on Jul. 17, 2017, and entitled "Apparatus for Diagnosis of Ocular Surface Disease." Such applications are incorporated by reference as if fully set forth herein.

BACKGROUND OF THE INVENTION

Ocular surface disease is a broad term that describes disorders of the surface of the cornea of the eye. These diseases include dry eye syndrome, meibomian gland dysfunction, blepharitis (eyelid inflammation), allergies, scarring from glaucoma medications, burns such as chemical or thermal burns, rosacea, allergies, and immunological conditions such as mucous membrane pemphigoid and Sjorgren's syndrome. These diseases can impact quality of life, and in some cases can severely affect eyesight, even resulting in blindness due to corneal scarring. These diseases often go undiagnosed and thus untreated, however, due to a lack of understanding of symptoms and inaccurate evaluation. Many patients simply feel that dry eyes at the end of the day are a "normal" occurrence and therefore do not seek medical attention. Nevertheless, early diagnosis is critical to effective treatment of many forms of ocular surface disease. Since a number of the causes of ocular surface disease occur more frequently in the elderly, the disease will continue to impact a larger and larger proportion of the population as the average lifespan of the population increases.

Inefficient or insufficient blinking is associated with certain types of ocular surface disease such as dry eye syndrome. Blinking is what triggers the expression of meibum, an oily substance that prevents evaporation of the eye's tear film and also prevents tear spillage onto the cheek. Blinking is also critical to the redistribution of essential nutrients in the tear film. Without a proper and complete blink at regular intervals, the meibum sits stagnant and thickens at the gland orifice from which it is secreted. Eventually gland blockage can occur, which leads to gland atrophy. Some current research indicates that the long-term viewing of electronic video displays, computers, electronic tablets, smartphones, and other such devices may lead to poor blinking habits, thus increasing ocular surface disease in an age when a large proportion of the population is viewing these devices for many hours per day.

Currently, diagnosis of ocular surface disease occurs, if at all, during a routine eye and vision examination. A more in-depth evaluation of the ocular surface and adjoining adnexa may be performed based on the patient's history, an assessment of associated risk factors, and examination of the anterior ocular structures and their functions. This often follows specific complaints by the patient, such as burning or stinging in the eyes, scratchiness, irritation, increased mucous, or reduced contact lens tolerance. By the time these factors are present, however, the disease may be well progressed. The prior art lacks a simple and effective method of diagnosis of this disease that can be performed routinely and inexpensively in a typical clinical setting in order to achieve an earlier diagnosis of ocular surface disease, and thus lead to a treatment that is more likely to be efficacious and less invasive for the patient.

Any references mentioned in this background section are not admitted to be prior art with respect to the present invention.

BRIEF SUMMARY OF THE INVENTION

The present invention is directed to a device that is used for the treatment of ocular surface disease. The device includes a display screen that presents text or other visual elements to the patient as part of a visual test. While the patient is viewing the display, a camera that is incorporated into the device records a video of the patient's eye movements, and while doing so tracks the number and quality of blinks that occur in the patient's eyes during the test. Software and an accelerometer incorporated into the device provide a visual cue to ensure that the display of the device (and the camera) is oriented at the appropriate angle to the patient's eyes for proper blink detection. The device in certain embodiments includes functionality allowing the diagnosing physician to replay the video of the patient's blinking at various speeds and resolutions for a more accurate diagnosis of both full blinks and partial blinks. The results of the test with the device are combined with answers provided by the patient to create an estimated blink performance. This estimated blink performance is used to create a suggested treatment regimen for patients who may exhibit ocular surface disease such as dry eye syndrome.

These and other features, objects and advantages of the present invention will become better understood from a consideration of the following detailed description in conjunction with the drawings as described following:

DETAILED DESCRIPTION OF THE PREFERRED EMBODIMENT(S)

Figure 1:
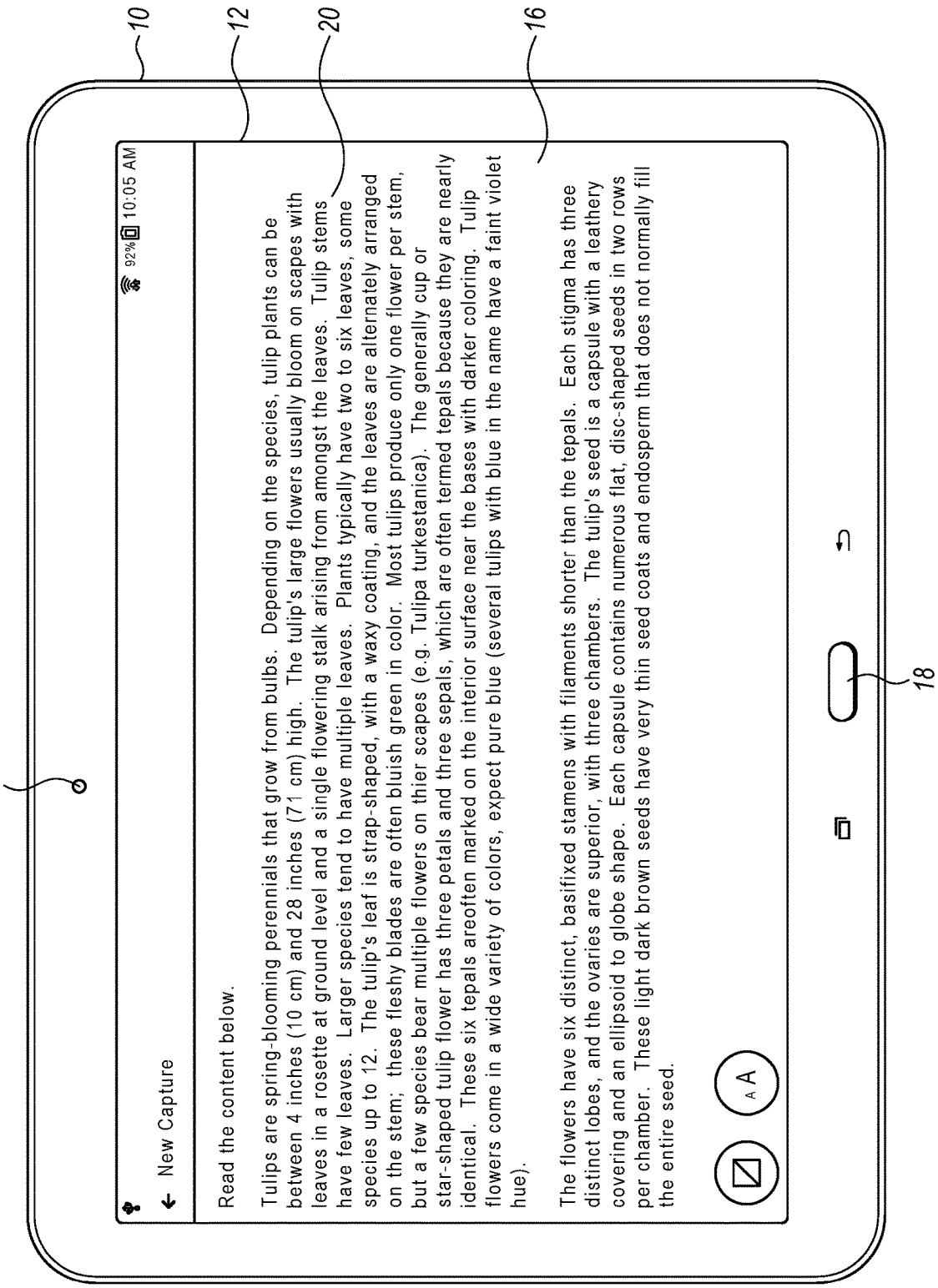
FIG. 1 is a top plan view of an embodiment of the invention.

Referring to FIG. 1, a device according to an embodiment of the invention may be described. The hardware for device 10 may be an electronic tablet, various types of which are known in the art. Device 10 includes an electronic display 12 and a forward-facing camera 14. The display 12 is capable of displaying text 16 or other visual material. Preferably, display 12 is a touchscreen display. A physical button 18 may be used for control of the device 10 as well as virtual buttons, sliders, and other controls presented on touchscreen display 12. In one embodiment, device 10 may be a Galaxy Tab 4 manufactured by Samsung Corporation. This electronic tablet possesses sufficient processing power to perform the required functions, sufficient storage to download and store the software "app" used for testing, is reasonably inexpensive, and also features a forward-facing camera 14 that possesses sufficient resolution for testing.

The camera of the Galaxy Tab 4 also offers the advantage that it is positioned to be operated in a landscape orientation. Most commercial tablets have the camera at the top of the screen when in portrait mode (taller than wider), rather than the camera at the top or bottom when in landscape mode (wider than taller). The configuration with the camera 14 at the top or bottom when in landscape orientation is preferred because operating the device in landscape orientation provides improved results in detecting eye movement. The image to be viewed by the patient may be made larger left to right, with the camera still positioned almost directly in front of the patient. If a device with a camera at the top (in portrait mode) were used such as an Apple iPad, the offset could possibly cause an obscuring angle on the opposite eye of the patient. If, for example, the camera were at the left side of the display when turned to landscape mode, then the offset could cause an obscuring angle with respect to the right eye of the patient. The camera 14 need not be positioned precisely at the middle of electronic display 12, as long as it is sufficiently near the middle that there is no obscuring angle created with respect to either of the patient's eyes. For purposes herein, "near" the middle means sufficiently close to the middle that no obscuring angle is created. The Galaxy Tab 4, for example, has a camera that is near the centerline but slightly offset.

Display outline 20 is used to ensure proper alignment of the device with respect to the patient's eyes, as will be described more fully below. The device 10 may be presented in a custom-designed case (not shown) to protect the device 10 during clinical use and to help facilitate proper usage of device 10 by providing a grip that naturally inclines the device to the appropriate angle between the patient's eyes and display 12. Handles extending to the left and right (in landscape mode) is one possible embodiment of the desired grip, with openings provided for the patient's thumb and fingers as the hand wraps around the grips aligned perpendicular to the direction of the text when in landscape mode.

Figure 2:
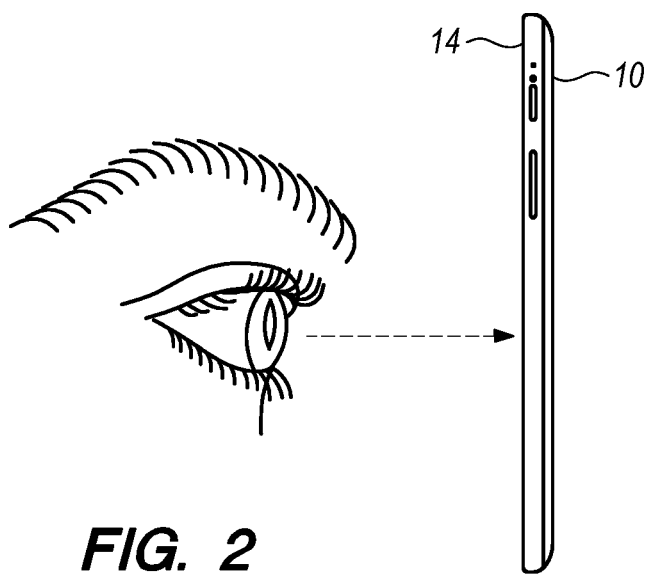
FIG. 2 is a side elevational view of an embodiment of the invention when properly aligned for use when performing a diagnosis on a patient, the drawing also showing the patient's eyes in alignment with the device.

Turning now to FIG. 2, operation of device 10 in the diagnosis of ocular surface disease may be described. The principle of operation is that the patient is presented text 16 on display 12. The reading passage of text 16 may be chosen from any reading material, the precise words not being critical to the diagnosis. The patient may adjust the contrast of the screen and the size of the letters for comfort, using controls presented on device 10 including touchscreen display 12. Optionally, the patient may be given a preliminary screen on which to select a desired reading topic in order to provide further patient comfort during the test.

Figure 3:
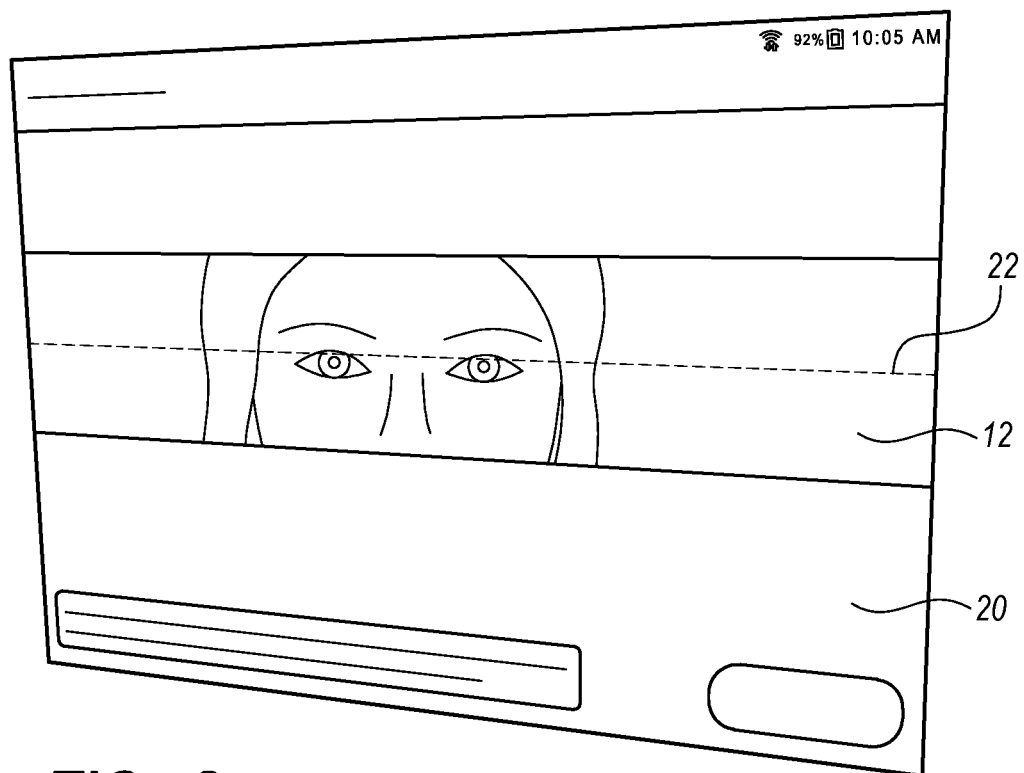
FIG. 3 is a view of an electronic display of an embodiment of the invention when used during the eye alignment phase.

To begin the test, the patient must align his or her eyes with display 12 of device 10. The software "app" installed on device 10 that facilitates the diagnostic testing utilizes the built-in accelerometer and gyroscope in device 10 to position the screen at a 90 degree angle and parallel to the patient, and detect any deviations from this angle. The device presents an alignment screen to the patient in order to facilitate alignment, as shown in FIG. 3. The alignment screen uses forward-facing camera 14 to show the patient an image of him- or herself on display 12 so that the eye position relative to the device 10 can be easily gauged by the patient. Superimposed over the patient's image is horizontal alignment line 22. The patient is instructed, by an on-screen prompt, to align his or her eyes on the line 22. The software displays a red outline 20 around display 12 until the patient properly aligns the device 10 for the test, at which time the outline 20 on display 12 turns to green to indicate that alignment is completed. Other types of alignment indicators could be used in alternative embodiments, such as, for example, changing the color tint of the entire image viewed by the patient on display 12.

Once alignment occurs, the next screen is displayed as shown in FIG. 1 and previously described, and the patient then reads the text passage 16 for a period of time. In one embodiment that period being equal to or less than sixty seconds, and in one particular embodiment being twenty seconds. Other test images could be used in place of text passage 16 to draw the patient's visual attention during the test period. The purpose of the text or other test images is to draw the patient's attention so that natural blinking may be observed and recorded.

Figure 4:
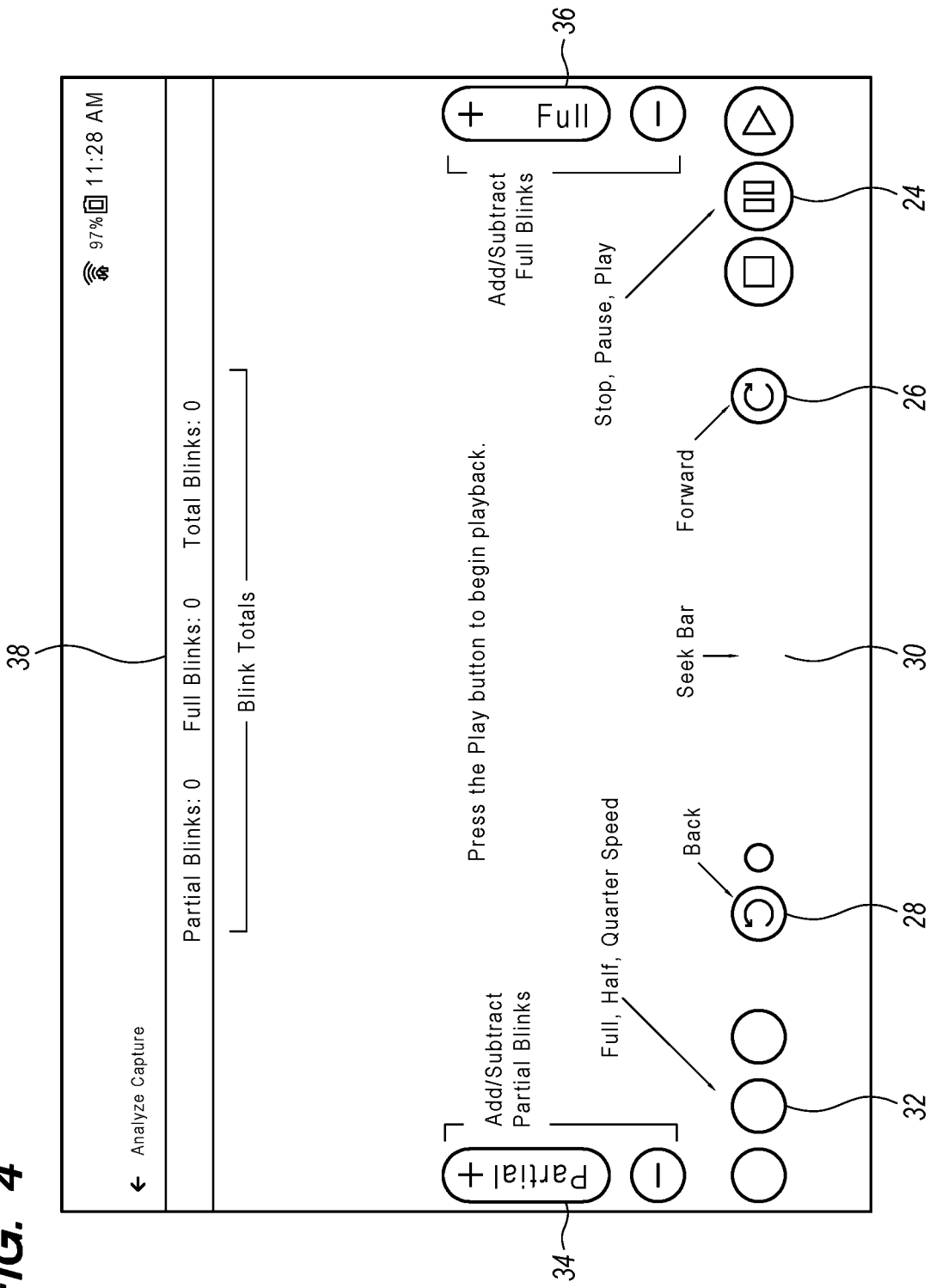
FIG. 4 is a view of an electronic display of an embodiment of the invention when used during the video replay phase.

During the time that the patient is reading text passage 16, camera 14 in conjunction with the software app is recording a video of the patient's eyes. The software embedded in the device creates a buffer space in memory where this video is stored. The app also measures and records the quantity and quality of blinks during the test. After the test is complete, the physician performing the diagnosis may review this video using a screen on display 12, such as shown in FIG. 4. The app allows the physician to alter the video resolution (such as doubling the size of the image) and replay the image at multiple speeds, including, in certain embodiments, real-time speed, one-half speed, and one-fourth speed. This may be performed, in certain embodiments, with on-screen controls. Playback controls 24 may include stop, pause, and play on-screen buttons. This allows the diagnosing physician to carefully count the number of full blinks and, optionally, the number of partial blinks of the patient during the test, and further to evaluate the quality of any partial blinks. Two different sets of counters may be embedded in the software to count both full and partial blinks automatically, with the ability of the physician to override the automated results based on visual inspection of the video during playback. Partial blinks may be incremented or deleted with on-screen partial blink control 34, with full blinks similarly measured using on-screen full blink control 36. A slider bar 30 may be used to quickly move forward or backward in the recorded video, in conjunction with back button 28 and forward button 26. Magnification is controlled with magnification buttons 32. The current blink totals are shown in blink display bar 38 at the top of display 12.

After the data is reviewed, the physician may, by activation of controls such as button 18 and on-screen buttons on touchscreen display 12, erase the data stored in the data buffer of device 10 and thus reset the system for testing with another patient.

The data gathered from the test performed with device 10 is analyzed along with questions asked of the patient by the physician in order to arrive at a final diagnosis. This diagnosis may be aided by a second software program executing on a remote server at the clinical site, or accessible through the cloud in a "Software as a Service" (SaaS) model at the clinical site from the remote server. In one implementation, the app on device 10 interacts directly with the remote software to provide a blink capacity score calculated during a patient's test. The number of full blinks and the number of partial blinks may feed into the calculation performed at the remote software. For example, suppose that a patient exhibits five full blinks and five partial blinks during the evaluation. The remote program would include a setting for the normal or average blink rate while reading, which may be 15 (more precisely, 14.9), although any value could be used as determined. The remote program may further assess each partial blink as only being partially as effective as a full blink, such as, for example, 25% as effective. Therefore, the remote program would calculate the patient's blink capacity in this example as ((5×0.25)+(5×1))/15=0.417, or approximately 41.7%. With knowledge of this blink capacity indicator, the physician may more accurately diagnose and treat the patient. For example, if a patient has also been diagnosed using meibography (the imaging of the Meibomian glands) with a score of grade 1, then certain treatments may not be needed immediately if the patient exhibits a blink capacity of more than 75%; on the other hand, a patient with a score of grade 1 on the meibography imaging and a blink capacity score as low as the one provided in this example may need treatment earlier or even immediately, because the lack of blinking coupled with this score makes the treatment intervention a more immediate concern.

In certain variations, the patient may take the tests described herein multiple times, and the results of all of those tests may be taken into account by a diagnostic algorithm in order to better identify any eye disease experienced by the patient, and in order to better develop a treatment regime for the patient. The diagnostic algorithm may include the use of artificial intelligence (AI) programming methods, whereby as additional data is brought into the algorithm it "learns" from this data and is able to provide a better diagnosis as more data is accumulated. Likewise, the diagnostic algorithm in certain variations may be exposed to other patient data that is relevant to the eye disease diagnosis to aid in its determination of a proper treatment regime. Still further, the diagnostic algorithm may utilize data from a number of patients, each of whom may have taken the blink test multiple times, along with other pertinent data about these patients, in order to "learn" even better and thereby provide the most accurate diagnosis for each patient. It may be seen that in this way the diagnostic method using the blink measuring apparatus will yield improved results as the universe of patients who have taken the test grows, and as each patient takes the test additional times.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. When a grouping is used herein, all individual members of the group and all combinations and subcombinations possible of the group are intended to be individually included in the disclosure. All references cited herein are hereby incorporated by reference to the extent that there is no inconsistency with the disclosure of this specification. If a range is expressed herein, such range is intended to encompass and disclose all sub-ranges within that range and all particular points within that range.

The present invention has been described with reference to certain embodiment(s) that are intended to be exemplary only and not limiting to the full scope of the present invention, which is limited only by the scope of the following claims.

The invention claimed is:

1. A method for diagnosing ocular surface disease in a patient's eyes using an electronic display device executing a software app, the method comprising the steps of:
   a. displaying a first screen to the patient, the first screen comprising an alignment indicator, wherein the alignment indicator comprises a first indicia when the display device is properly aligned with the patient's eyes, and comprises a second indicia when the display device is not properly aligned with the patient's eyes;
   b. displaying a second screen to the patient, the second screen comprising a test material for viewing by the patient;
   c. recording a video of the patient's eyes while the patient is viewing the test material of the second display screen;
   d. using the software app, measuring the quality and quantity of blinks by the patient's eyes while the patient is viewing the test material of the second display screen;
   e. displaying a third display screen to a diagnosing physician, wherein the third display comprises the video of the patient's eyes while viewing the test material of the second display screen.

2. The method of claim 1, further comprising the step of displaying a set of controls to the diagnosing physician on the third screen, and receiving control inputs from the diagnosing physician.

3. The method of claim 2, wherein the quality of blinks measured using the software app comprises the number of partial blinks and the number of full blinks while the patient is viewing the test material, and the quantity of blinks measured using the software app comprises the total number of blinks while the patient is viewing the test material.

4. The method of claim 3, wherein the control inputs from the diagnosing physician comprise modifications to one or more of the number of partial blinks, the number of full blinks, and the total number of blinks.

5. The method of claim 4, further comprising the steps of:
   a. sending blink data from the software app to a remote software program executing at a remote server in communication with the electronic display device, wherein the blink data comprises a count of partial blinks and a count of full blinks; and
   b. calculating at the remote software program a blink capacity based on the blink data.

6. The method of claim 5, wherein the step of recording a video of the patient's eyes while the patient is viewing the test material of the second display screen is performed a plurality of times over a plurality of separate visits by the patient to a facility where the recording takes place, and further comprising the steps of:
   a. aggregating a data set from the multiple recordings;
   b. combining the data set from the multiple recordings with other patient data to create a comprehensive view of the patient's eye health; and
   c. applying a diagnostic algorithm to the comprehensive view of the patient's eye health to create an eye disease diagnosis specific to the patient.

7. The method of claim 6, wherein the eye disease diagnosis comprises identification of at least one medication for the treatment of the patient.

8. The method of claim 7, wherein the medication is a prescription medication.

9. The method of claim 7, wherein the medication is an over-the-counter medication.

10. The method of claim 6, wherein the step of recording a video of the patient's eyes while the patient is viewing the test material of the second display screen a plurality of times over a plurality of separate visits by the patient is performed for a plurality of patients, and wherein the step of applying a diagnostic algorithm to the comprehensive view of the patient's eye health to create an eye disease diagnosis specific to the patient is performed for the plurality of patients and each use of the diagnostic algorithm draws from data collected about all of the plurality of patients.

11. A method for diagnosing ocular surface disease in a patient, the method comprising the steps of:
- on an electronic device comprising a display screen and a camera, displaying an alignment indicator to the patient;
- using the camera, capturing a video stream of a set of eyes of the patient;
- on the electronic device, displaying the video stream so that the video stream is viewable by the patient;
- using the alignment indicator on the electronic device, providing an alignment signal to the patient indicative of whether the pair of eyes of the patient are aligned with the electronic device;
- after the patient has aligned the electronic device using on the alignment signal, displaying on the display screen a reading passage of text to the patient; and
- using the video stream of the set of eyes of the patient, measuring at the electronic device a blink quantity and a blink quality while the patient is reading the reading passage of text.

12. The method of claim 11, wherein the step of displaying an alignment indicator to the patient comprises the step of displaying an outline circumscribing the display screen.

13. The method of claim 11, wherein the step of displaying an alignment indicator to the patient comprises the step of displaying a horizontal alignment line on the display screen.

14. The method of claim 11, wherein the step of displaying an alignment indicator to the patient comprises the step of displaying the alignment indicator in a red color when the set of eyes of the patient and the display screen are not aligned, and displaying the alignment indicator in a green color when the set of eyes of the patient and the display screen are aligned.

15. The method of claim 11, further comprising the steps of:
- on the display screen, displaying a selection screen comprising a plurality of options for a subject matter of the body of text; and
- receiving an input from the patient at the electronic device to select the subject matter of the body of text.

16. The method of claim 11, further comprising the step of, on the display screen, displaying an analysis screen comprising a replay of the video stream recorded while the patient is viewing the reading passage of text.

17. The method of claim 16, wherein the analysis screen further comprises on-screen blink controls to mark a blink quality value and a blink quantity value, and further comprising the step of receiving from a physician viewing the analysis screen a blink input at the on-screen blink controls to denote the blink quality value and the blink quantity value.

18. The method of claim 17, wherein the analysis screen further comprises on-screen magnification controls, and further comprising the step of receiving from a physician viewing the analysis screen a magnification input at the on-screen magnification controls to alter a magnification of the video stream.

19. The method of claim 11, further comprising the steps of:
- at a remote software application executing on a remote server linked to the electronic device by an electronic communications network, receiving a set of blink data comprising the blink quality value and the blink quantity value from the electronic device; and
- calculating from the set of blink data a blink capacity for the patient.

* * * * *